US011135111B2

(12) United States Patent
Hillenbrand, II et al.

(10) Patent No.: US 11,135,111 B2
(45) Date of Patent: *Oct. 5, 2021

(54) PATIENT MONITORING AND REPOSITIONING SYSTEM AND RELATED METHOD

(71) Applicant: Hillenbrand Management Company LLC, Batesville, IN (US)

(72) Inventors: William A. Hillenbrand, II, Batesville, IN (US); David Hornbach, Brookville, IN (US); Joseph Kummer, Cincinnati, OH (US); Timothy Savage, Batesville, IN (US)

(73) Assignee: Hillenbrand Management Company LLC, Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/783,514

(22) Filed: Feb. 6, 2020

(65) Prior Publication Data

US 2020/0170858 A1 Jun. 4, 2020

Related U.S. Application Data

(60) Continuation of application No. 16/284,208, filed on Feb. 25, 2019, now Pat. No. 10,568,791, which is a
(Continued)

(51) Int. Cl.
*A61G 7/057* (2006.01)
*A61B 5/11* (2006.01)
(Continued)

(52) U.S. Cl.
CPC ............ *A61G 7/057* (2013.01); *A61B 5/1113* (2013.01); *A61B 5/1116* (2013.01);
(Continued)

(58) Field of Classification Search
CPC .... A61G 7/057; A61G 7/1026; A61G 7/1065; A61G 7/0527; A61G 2203/44; A61B 5/1116
See application file for complete search history.

(56) References Cited

U.S. PATENT DOCUMENTS

| | | |
|---|---|---|
| 1,877,610 A | 9/1932 | Steiner |
| 2,827,642 A | 3/1958 | Huff |

(Continued)

OTHER PUBLICATIONS

European Patent Office, European Search Report issued in corresponding European Patent Application No. EP15760833.2 dated Sep. 4, 2017, 6 pages.

(Continued)

*Primary Examiner* — Eric J Kurilla
(74) *Attorney, Agent, or Firm* — Wood Herron & Evans LLP

(57) ABSTRACT

A patient monitoring and repositioning system includes a mattress, a sheet residing on an upper surface of the mattress, a housing containing a drive mechanism, and a sensor adapted to sense a position of a patient resting on the mattress. The drive mechanism is operable to pull the sheet and thereby pull the patient resting thereon. The housing receives the sheet through a slot. In the event that the patient is in an undesirable position on the mattress as detected by the sensor, a controller directs the drive mechanism to pull the sheet so as to pull the patient thereon from the undesirable position to a desirable, predetermined position. The controller may direct the drive mechanism automatically or indicate the undesirable position to a caregiver so that the caregiver may direct the drive mechanism accordingly.

17 Claims, 8 Drawing Sheets

Related U.S. Application Data division of application No. 15/121,230, filed as application No. PCT/US2015/020489 on Mar. 13, 2015, now Pat. No. 10,258,525.

(60) Provisional application No. 61/952,380, filed on Mar. 13, 2014.

(51) Int. Cl.
*A61G 7/10* (2006.01)
*A61G 7/05* (2006.01)
*A61B 5/00* (2006.01)

(52) U.S. Cl.
CPC .......... *A61B 5/6891* (2013.01); *A61B 5/6892* (2013.01); *A61G 7/05* (2013.01); *A61G 7/0527* (2016.11); *A61G 7/1026* (2013.01); *A61G 7/1065* (2013.01); *A61B 2562/043* (2013.01); *A61G 2203/30* (2013.01); *A61G 2203/44* (2013.01)

(56) References Cited

U.S. PATENT DOCUMENTS

| | | | |
|---|---|---|---|
| 3,597,774 | A | 8/1971 | Warren |
| 3,829,914 | A | 8/1974 | Treat |
| 4,025,973 | A | 5/1977 | Walbrecht |
| 4,799,273 | A | 1/1989 | Elze |
| 4,819,283 | A | 4/1989 | DiMatteo et al. |
| 4,926,513 | A | 5/1990 | Oats |
| 4,941,220 | A | 7/1990 | DiMatteo et al. |
| 5,016,306 | A | 5/1991 | Grivna et al. |
| 5,127,113 | A | 7/1992 | Di Matteo et al. |
| 5,184,112 | A | 2/1993 | Gusakov |
| 5,280,657 | A | 1/1994 | Stagg |
| 5,718,009 | A | 2/1998 | Lin |
| 5,901,388 | A | 5/1999 | Cowan |
| 6,282,734 | B1 | 9/2001 | Holberg |
| 6,629,323 | B2 | 10/2003 | Sverdlik et al. |
| 6,662,388 | B2 | 12/2003 | Friel et al. |
| 7,003,819 | B2 | 2/2006 | Weigand |
| 7,111,338 | B2 | 9/2006 | Faux et al. |
| 7,337,478 | B1 | 3/2008 | Lake |
| 7,434,278 | B2 | 10/2008 | White et al. |
| 7,725,964 | B2 | 6/2010 | Minning et al. |
| 8,156,582 | B2 | 4/2012 | Rupar et al. |
| 9,192,535 | B2 | 11/2015 | Sverdlik et al. |
| 9,205,012 | B2 | 12/2015 | Hillenbrand, II et al. |
| 10,258,525 | B2 * | 4/2019 | Hillenbrand, II ..... A61B 5/1116 |
| 10,568,791 | B2 * | 2/2020 | Hillenbrand, II .... A61B 5/6891 |
| 2002/0083521 | A1 | 7/2002 | Sverdlik et al. |
| 2005/0217023 | A1 | 10/2005 | Tally |
| 2006/0273292 | A1 | 12/2006 | Milam |
| 2009/0178193 | A1 | 7/2009 | Jewell et al. |
| 2010/0281613 | A1 | 11/2010 | Hillenbrand, II |
| 2011/0263950 | A1 | 10/2011 | Larson et al. |
| 2012/0139395 | A1 | 6/2012 | Dietrich |
| 2012/0144581 | A1 | 6/2012 | Roberg |
| 2012/0299353 | A1 | 11/2012 | Griswold et al. |
| 2013/0025048 | A1 | 1/2013 | Pruett |
| 2013/0160208 | A1 | 6/2013 | Davenport et al. |
| 2014/0259389 | A1 | 9/2014 | Hillenbrand, II et al. |
| 2015/0143628 | A1 | 5/2015 | Fowler et al. |
| 2017/0020756 | A1 | 1/2017 | Hillenbrand, II et al. |
| 2017/0216117 | A1 | 8/2017 | Rigoni et al. |
| 2019/0070053 | A1 | 3/2019 | Tarakanova |

OTHER PUBLICATIONS

European Patent Office, Supplemental Search Report issued in corresponding European Patent Application No. EP15760833.2 dated Sep. 21, 2017, 1 page.
International Bureau of WIPO, Notification of Transmittal, International Preliminary Report on Patentability issued in International Application No. PCT/US2015/020489, dated Sep. 13, 2016, 5 pgs.
International Searching Authority, Notification of Transmittal, International Search Report and Written Opinion issued in International Application No. PCT/US2015/020489, dated Jun. 22, 2015, 7 pgs.
International Searching Authority, Search Report and Written Opinion issued in corresponding International Application No. PCT/US15/20489 dated Jun. 22, 2015.

* cited by examiner

PATIENT MONITORING AND REPOSITIONING SYSTEM AND RELATED METHOD

CROSS-REFERENCE TO RELATED APPLICATIONS

This application is a continuation of U.S. patent application Ser. No. 16/284,208, filed Feb. 25, 2019 which is a divisional of U.S. patent application Ser. No. 15/121,230, filed Aug. 24, 2016 (now U.S. Pat. No. 10,258,525) which is a U.S. National Phase Application of International Application No. PCT/US15/20489, filed Mar. 13, 2015 which claims the benefit of U.S. Provisional Patent Application No. 61/952,380, filed on Mar. 13, 2014, the disclosures of which are incorporated by reference herein in their entirety.

Applicant's U.S. patent application Ser. No. 13/837,185, filed Mar. 15, 2013 (now U.S. Pat. No. 9,205,012) (hereinafter "the '012 patent") is also expressly incorporated by reference herein, in its entirety.

FIELD OF THE INVENTION

The present invention relates to patient repositioning and, more particularly, to a system that reduces and relieves interface pressures between a patient and a bed support surface by reducing concentrated forces on the patient, such as friction and shear forces, in order to reduce the likelihood of discomfort, pressure ulcers, and/or other injuries to the patient.

SUMMARY OF THE INVENTION

Applicant's '012 patent discloses various details and embodiments of a patient repositioning system wherein the system moves a sheet and the patient supported thereon toward a head end of the bed, such as a healthcare bed that articulates to improve patient comfort. The '012 patent discloses numerous features and details related to the general concept of patient repositioning in this manner, such as the sheet having a width greater than that of the mattress.

Nonetheless, the '012 patent focuses on reducing and simplifying the efforts needed by a caregiver to reposition a patient toward a head end of the bed. Generally, the caregiver repositions the patient by physically activating the inputs to the system, and those inputs are part of, or at least associated with, a sheet receiver located partially below the top surface of the mattress.

The present disclosure focuses on additional aspects of the patient repositioning system shown in the '012 patent. That is, the present disclosure focuses on a patient monitoring and repositioning system for detecting and identifying the need to reposition a patient, prior to the actual repositioning of the patient via such a patient repositioning system. This feature is helpful in reducing the occurrence of pressure ulcers with the patient, which could otherwise be caused by the patient remaining in an undesirable position rather than a desirable, predetermined position on the mattress. According to various embodiments of the patient monitoring and repositioning system disclosed herein, there is no need for a caregiver to be physically present, next to the bed, to detect that a patient has migrated down in the bed to an undesirable position and needs to be repositioned to a desirable position, which may also be referred to herein as a predetermined position or a normal position. Rather, the need for repositioning can be communicated to the caregiver via an alarm and/or some other indicator or call system, or it could be addressed automatically at the bed, with or without an alarm or indicator.

Once the need to reposition the patient has been detected, then that need can be addressed in any one of several ways. For example, the monitoring system can communicate to the repositioning system to automatically reposition the patient. Alternatively, the monitoring system can communicate the need for patient repositioning without prompting the repositioning system to automatically reposition the patient, such as requesting human intervention to reposition the patient at the bed-side, or requesting remote activation from a separate location, a central control station in another portion of the building, or even miles away at another location. In the context of this specification, a controller may be located on or near the bed or remotely from the bed for communicating with the bed via a wired or a wireless connection. With such remote patient repositioning capabilities and a plurality of such patient repositioning systems in place in a single facility, any desired number of such repositioning systems could be monitored and activated at the same time. Thus, any desired number of patients could be remotely repositioned at the same time, without requiring a like number of caregivers to interact with each repositioning system. However, for practical reasons, it may be that the actual patient repositioning is not performed remotely, but is instead initiated by a caregiver, or by the patient, who is physically present. But even in that case, the caregivers can be more efficient with their available time, because the present system is capable of simultaneously detecting, identifying, and communicating the need for repositioning of patients to one or more caregivers. In other words, this disclosure focuses on the coupling of a monitoring system for detecting patient position with a repositioning system for repositioning the patient, so that ultimately the patient can be repositioned, whether remotely or with a caregiver physically present. In addition, the control system, such as a central control system in the form of a hospital information system, operatively connects to the patient monitoring and repositioning system. The control system may further monitor the patient not being in the predetermined position, a time that the patient is not in the predetermined position, an amount of patient repositionings, a frequency of patient repositionings in a facility, an amount of sheet already used, a need to change or reset the sheet on the bed, a distance migrated by the patient on the bed, a time of the patient in each position on the bed, a time delay before repositioning the patient on the bed, a duration of repositioning the patient on the bed, a position of the patient on the bed, a time of day the patient was repositioned, and a frequency of patient repositionings executed on the bed.

According to one aspect of a patient monitoring and repositioning system of the type disclosed herein, each of a plurality of patient repositioning systems (of the type disclosed in the '012 patent) is preferably equipped with a sensor arrangement for sensing the position of the patient. The sensor arrangement could employ one or more load cells, infrared beams, capacitors, resistors, cameras with image detection, magnets, or any other type of structure for sensing the position of the patient on the mattress (e.g., acoustic, sonar, ultrasonic, etc.).

According to another aspect of the invention, with the sensor arrangement in place, and operatively connected to the drive mechanism, and the sensor arrangement also operatively connected to an alarm and/or a control system, the monitoring system senses when the patient has moved toward the foot end of the bed. More particularly, the sensor arrangement senses substantially the entire top surface of the mattress for sensing patient movement. When such patient moves toward the foot end from the desirable position to the undesirable position, and the sensor arrangement detects and signals that the patient has moved toward the foot end of the bed, the monitoring system automatically requests the repositioning system to reposition the patient and/or uses an indicator, such as an alarm, to communicate the need to reposition the patient to the caregiver. As such, the indicator operatively indicates the position of the patient relative to the mattress at all times during use. Any one or more of a number of different types of visual and/or audible indicators may be used. For example, the indicator may be a display, one or more LEDs, a graphic display message, an audible signal, a wired transmission message, a wireless transmission message, and/or a parallel or serial message. Thereafter, the patient can be repositioned toward the head end of the bed automatically or either via remote actuation of the drive mechanism without a caregiver physically present proximate to the bed, or via actuation of the drive mechanism by the caregiver who is physically present proximate to the bed via a user interface. This repositioning can then also be detected by the monitoring system to indicate that a logical sequence of events has been completed, and that the patient is in the predetermined position. Once the patient has been restored to the predetermined position, the monitoring system ceases to indicate and/or communicate the need to reposition the patient. The monitoring system may alternatively or additionally communicate that the patient was repositioned.

Still further, with a plurality of such patient monitoring and repositioning systems of this type in use in a facility, and operatively connected to a central control station, the central control station can enable the operator of the facility to monitor various events and parameters, including the patient not being in the predetermined position, a time that the patient is not in the predetermined position, an amount of patient repositionings, a frequency of patient repositionings in a facility, an amount of sheet already used, a need to change or reset the sheet on the bed, a distance migrated by the patient on the bed, a time of the patient in each position on the bed, a time delay before repositioning the patient on the bed, a duration of repositioning the patient on the bed, a position of the patient on the bed, a time of day the patient was repositioned, and a frequency of patient repositionings executed on the bed.

In use, according to an exemplary embodiment, the patient rests on a mattress, but slides from the predetermined position toward the foot end of the bed to an undesirable position. The sensor arrangement detects the undesirable position of the patient and identifies the need to reposition the patient from the undesirable position to the predetermined position. A controller, operatively connected to the sensor arrangement, automatically directs the drive mechanism to pull the sheet toward the head end and, in turn, return the patient to the predetermined position. Alternatively, according to another exemplary embodiment, the controller, operatively connected to the sensor arrangement, is further connected to an indicator, such as an audible alarm. The controller activates the audible alarm in order to indicate to a caregiver that the patient has moved to an undesirable position. In turn, the caregiver operatively actuates the drive mechanism to pull the sheet toward the head end and, in turn, return the patient to the predetermined position. The caregiver may operatively actuate the drive mechanism by interacting with a user interface proximate to the bed or by remotely directing the drive mechanism. In turn, the audible alarm is deactivated to signal that the patient is in the desirable position. By way of example, the above scenarios may be completed by the patient repositioning system disclosed in the '012 patent in conjunction with the patient monitoring and repositioning system described herein.

DETAILED DESCRIPTION OF THE INVENTION

Figure 1:
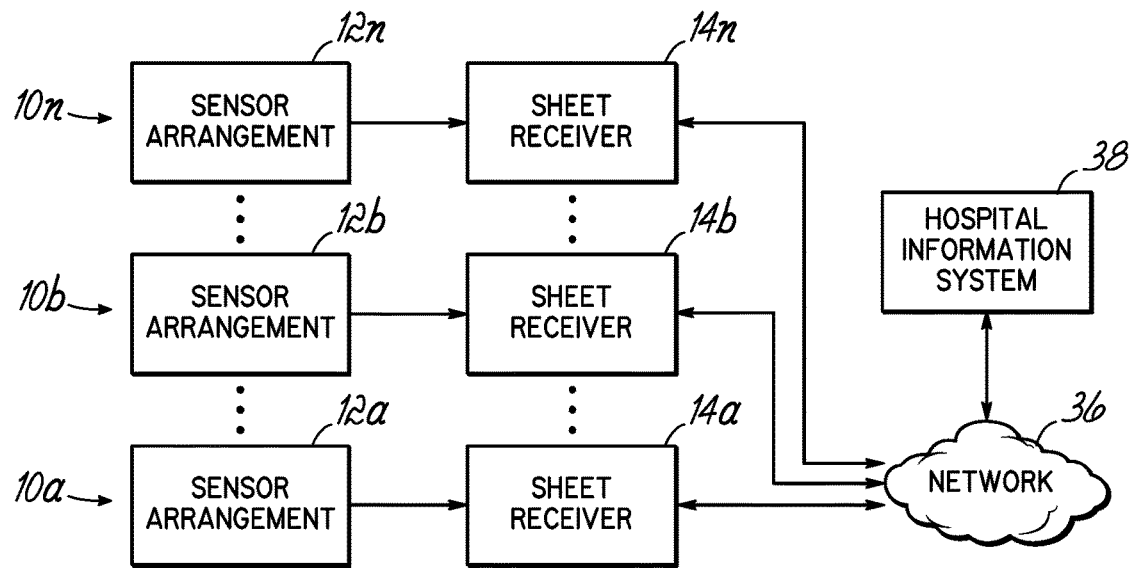
FIG. 1 is a diagram of a plurality of patient monitoring and repositioning systems operatively connected to a hospital information system via a network according to a first exemplary embodiment of the invention.

With reference to FIGS. 1-3B, a patient monitoring and repositioning system 10a includes a sensor arrangement 12a, a sheet receiver 14a, and a sheet 16 for use with a health care bed 18. The sensor arrangement 12a is more particularly a plurality of sensors 20 configured to detect a position of a patient 22 resting on the health care bed 18. The sensor arrangement 12a is at least one sensor 20, which senses the position of the patient 22 and indicates to a controller 24 whether or not the patient 22 is in a desirable, predetermined position relative to a mattress 26 of the health care bed 18. In the event that the patient 22 migrated along the mattress 26 to an undesirable position, which may also be referred to herein as not being in the predetermined position, the controller 24 automatically signals a drive mechanism 28 within a housing 29 of the sheet receiver 14a to pull the sheet 16 and, in turn, pull the patient 22 resting on the sheet 16 until the patient 22 returns to the predetermined position. As an alternative to automatic repositioning by the controller 24, the caregiver may direct the controller 24 to pull the sheet 16, such as in response to one or more indicators 30, 32, 34 described below in additional detail. As described herein, the term "predetermined position" means the desirable position and/or range of positions relative to the mattress 26 in which the patient 22, resting on the mattress 26, benefits from a reduced likelihood of injury, such as by pressure ulcers, and an increased likelihood of patient comfort. This desirable position and/or range of positions may refer to the patient's translational position relative to the mattress 26, the patient's rotational position relative to the mattress 26, or any combination thereof. To this end, the predetermined position may be an approximation based on a typical patient or tailored uniquely to a particular patient. Similarly, the term "undesirable position" generally refers to any patient position on the mattress 26 in which the patient 22 is not within the predetermined position. Furthermore, it will be appreciated that the term "sense" with respect to the sensor arrangement 12a may refer to actively sensing the patient 22 in both the predetermined position and the undesirable position or actively sensing the patient 22 in only one of the predetermined and undesirable positions. As such, the patient monitoring and repositioning system 10a may infer the patient position if the patient is not actively sensed by the sensor arrangement 12a. The term "sense" is thus not intended to be limited to only actively sensing the patients 22. Thus, according to one embodiment, the controller 24 continuously senses the position of the patient relative to the mattress 26 while the patient 22 rests on the mattress 26.

With respect to FIG. 1, a plurality of the patient monitoring and repositioning systems 10a, 10b, 10n may be operated within a single health care facility or throughout multiple health care facilities. Each of the patient monitoring and repositioning systems 10a, 10b, 10n includes respective sensor arrangements 12a, 12b, 12n and sheet receivers 14a, 14b, 14n. The sheet receivers 14a, 14b, 14n operatively connect to a network 36, which also operatively connects to a control system 38. The control system 38 is more particularly a central control system 38, such as a hospital information system 38. The hospital information system 38 may include a data information system, data management system, intranet, and/or software that interfaces with a hospital scheduling system, conventional web server, e-mail server, or any other software configured to indicate information concerning the patient monitoring and repositioning system 10a to the caregiver. The hospital information system 38 is typically a device that includes a processor, a memory, and a network interface and may commonly be referred to as a computer. From the hospital information system 38, one or more caregivers may receive indications of patient position, verify automatic repositioning of the patients by the patient monitoring and repositioning systems 10a, 10b, 10n, verify repositionings of the patient 22 by the caregiver located at the bedside and/or direct the patient monitoring and repositioning systems 10a, 10b, 10n to perform patient repositioning as desired. Thus, the sheet receivers 14a, 14b, 14n and the hospital information system 38 are configured to communicate back and forth via the network 36. It will be appreciated that any number of patient monitoring and repositioning systems 10a, 10b, 10n may be used in accordance with the principles discussed herein.

Figure 2:
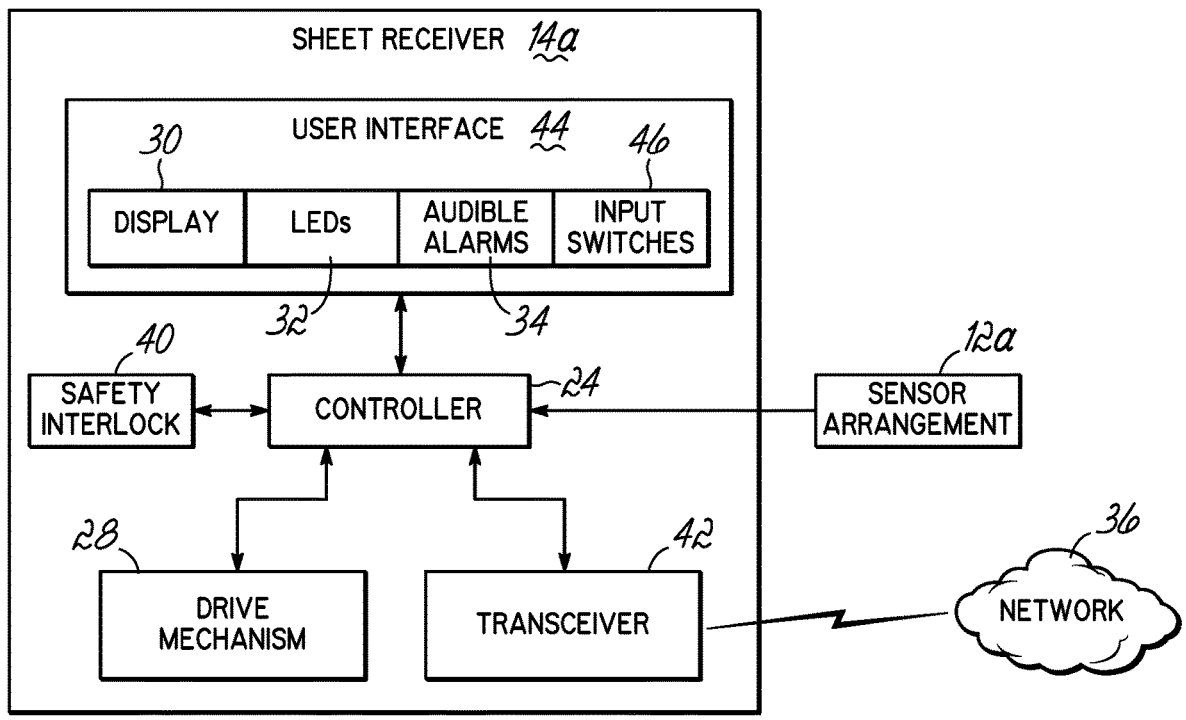
FIG. 2 is a diagram of a sheet receiver of a patient monitoring and repositioning system operatively connected to a network as shown in FIG. 1.
Figure 3A:
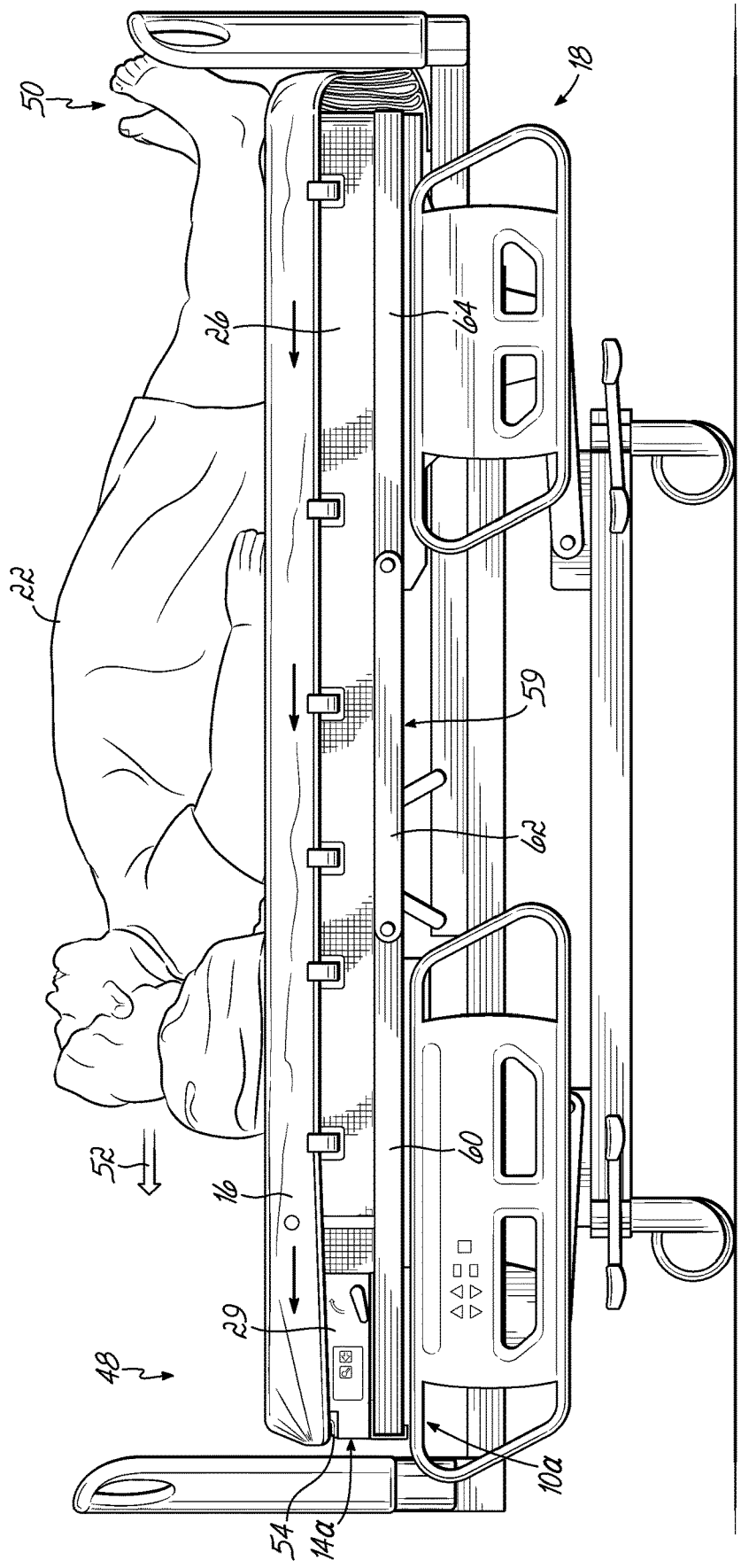
FIG. 3A is a side view of the patient monitoring and repositioning system of FIG. 1 with a patient in an undesirable position on a health care bed.
Figure 3B:
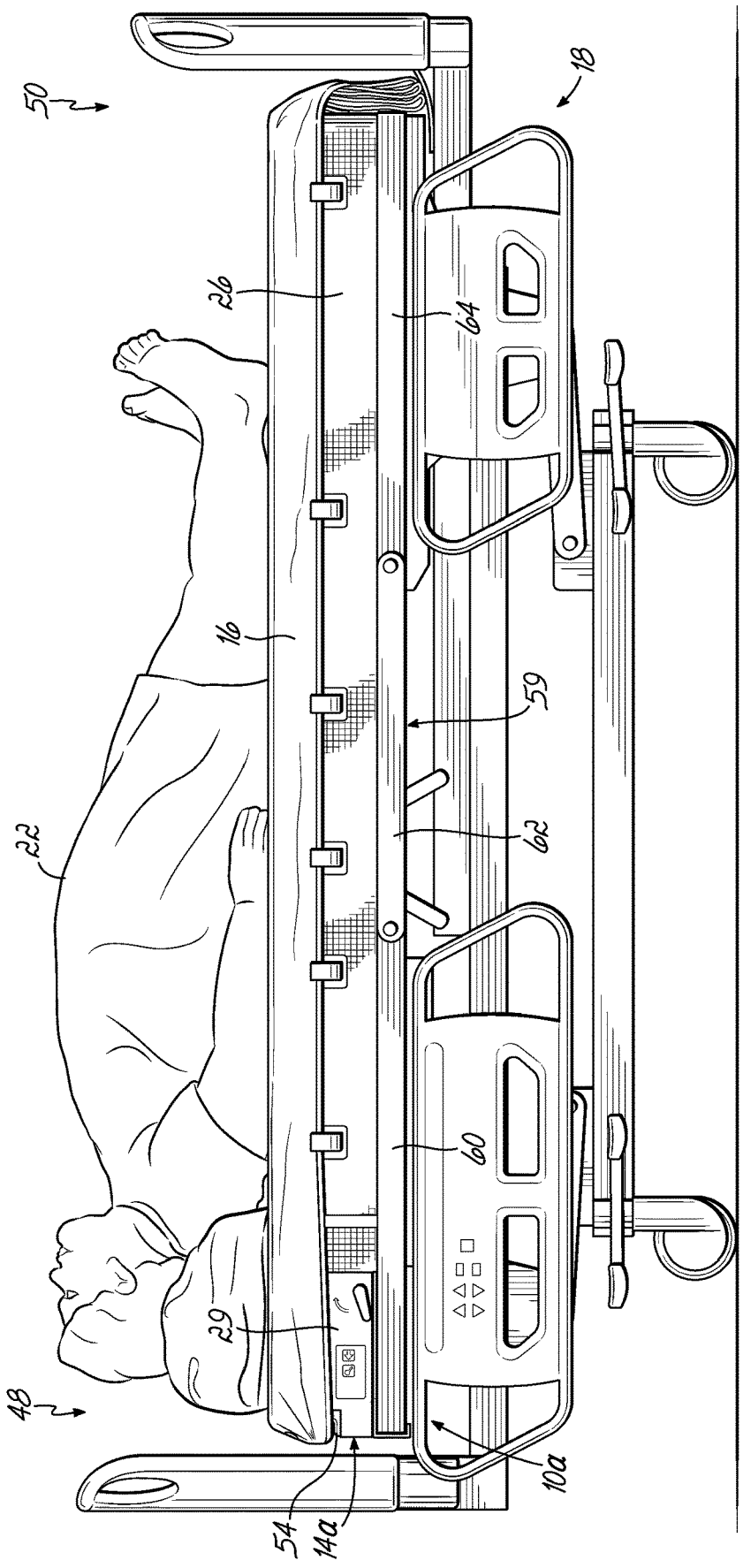
FIG. 3B is the side view similar to FIG. 3A, but with the patient in a desirable, predetermined position on the health care bed.

The sheet receiver 14a, as shown in FIGS. 2-3A, includes the controller 24 operatively connected to the drive mechanism 28, safety interlock 40, and a transceiver 42 contained within the housing 29. As shown, the controller 24 is in the sheet receiver 14a; however, the controller 24 may alternatively be positioned remotely from the sheet receiver 14a. The sheet receiver 14a also includes a user interface 44 operatively connected to the controller 24 and has the indicators 30, 32, 34 and input switches 46 configured for use by the caregiver to direct the controller 24. The indicators 30, 32, 34 are more particularly in the form of a display 30, such as a graphic touchscreen panel, one or more light emitting diodes ("LEDs") 32, and one or more audible alarms 34 for indicating information to the caregiver. In one embodiment, at least one of the indicators 30, 32, 34 is configured to indicate to the caregiver that the patient 22 is in the predetermined and undesirable positions. Alternatively, one of the indicators 30, 32, 34 may only indicate the position of the patient 22 when the patient 22 is either in the predetermined position or the undesirable position.

The transceiver 42 sends information to and receives information from the network 36 such that the controller 24 communicates with the hospital information system 38 (see FIG. 1). In some embodiments, the controller 24 may be a microprocessor or generally any processing computer device. The network 36 may include one or more networks, such as the Internet. In some embodiments, the network 36 may include one or more wide area networks (WAN) or local area networks (LAN). The network 36 may utilize one or more network technologies such as Ethernet, Fast Ethernet, Gigabit Ethernet, virtual private network (VPN), remote VPN access, a variant of IEEE 802.11 standard such as Wi-Fi, and the like. Communication over the network 36 takes place using one or more network communication protocols including reliable streaming protocols such as transmission control protocol (TCP). As such, the transceiver 42 is any device capable of communicating with both the controller 24 and the network 36, such as by the exemplary controllers and networks discussed briefly above. The above examples of the controller 24, the network 36, and the transceiver 42 are illustrative and not intended to limit the present invention.

The sensor arrangement 12a is positioned proximate to the mattress 26 so as to detect the patient 22 on the mattress 26 and communicate that detection to the controller 24 in order to indicate whether or not the patient 22 is in the predetermined position resting on the mattress 26 with the sheet 16 positioned therebetween. Specifically, the sensor arrangement 12a in conjunction with the controller 24 may be configured to determine the patient's translational position relative to the mattress 26, the patient's rotational position relative to the mattress 26, or any combination thereof. After receiving instructions automatically or manually from at least one of the user interface 44 and the hospital information system 38, the controller 24 directs the drive mechanism 28 to pull the sheet 16 only if the safety interlock 40 communicates to the controller 24 that the appropriate conditions exist for the repositioning of the patient 22. For example, the safety interlock 40 may include more than one lock out condition for preventing operation of the drive mechanism 28 by the controller 24, such as the bed head deck angle being too high, the sheet being improperly loaded, the absence of the patient 22 on the mattress 26, sheet contamination such as by a contamination sensor (e.g., high moisture content, soiling, bacteria presence, ascetic detection, image detection, etc.), and improper positions of a hinged access door 47 of the sheet receiver 14a. It will be appreciated that other lock out conditions may be used and, as such, the invention is not limited to the safety interlock 40 described herein.

With the conditions for repositioning the patient 22 determined to be appropriate by the controller 24 as signaled by the sensor arrangement 12a and the safety interlock 40, the controller 24 directs the drive mechanism 28 to pull the sheet

16. As discussed herein, the '012 patent describes one example of a patient repositioning system as follows:

The mattress for repositioning the patient generally includes the mattress foot end, the mattress head end, the upper surface, and the pair of longitudinal sides as described above. Generally, the pair of longitudinal sides is symmetric with a generally uniform thickness, while the upper surface has a substantially uniform width and length. The mattress is also covered in an outer ticking for effectively improving the life and comfort of the mattress. In addition, each of the retainers is attached to the outer ticking of the mattress in spaced relation along the length of the mattress longitudinal sides. However, the mattress head end also includes a head end section of reduced thickness relative to the generally uniform thickness of the remaining mattress. In this respect, the head end section is a relatively thin portion of the mattress and further includes a head end piece. The head end piece folds about a fold line relative to the rest of the mattress for improving access to the sheet receiver below the upper surface of the mattress head end. However, it will be appreciated that other respective portions of the mattress may be otherwise movable for accessing the sheet receiver.

Furthermore, at least a portion of the sheet receiver is positioned within a volume envelope of the mattress for effectively reducing an overall footprint of the mattress and sheet receiver. The reduced thickness of the head end section has a lower surface and a forward surface that collectively define the volume envelope that would otherwise be occupied by the mattress if not for the head end section of reduced thickness. Thereby, the head end section is complementary in shape to a housing of the sheet receiver.

The housing at least partially fits within the volume envelope against the lower surface and the forward surface of the head end section. The housing has a length substantially the same as the width of the mattress and includes a slot extending horizontally along the length of the housing. Additionally, the housing includes an extension protruding horizontally along the length of the housing and above the slot. According to an exemplary embodiment of the invention, the extension defines a lip against which the head end piece abuts when the sheet receiver is positioned within the volume envelope.

The housing of the sheet receiver includes an access door adjacent a top panel. The head end piece folds back at the fold line to expose the access door that hingedly connects to the housing. As such, the operator may move the access door by pivoting it up and against the mattress to open the sheet receiver. However, it will be appreciated that the access door may be movable in any way relative to the remainder of the sheet receiver to open the sheet receiver. For example, the access door may be unitary with or connected to the head end piece such that folding back the head end piece simultaneously opens the access door. The access door opens at the slot for reducing the number of openings into the housing. The open sheet receiver exposes each of the components within a sheet chamber defined by the housing. The sheet chamber includes a portion of the sheet receiver that may interact with the sheet, and thus, may require periodic cleaning by the operator.

In this respect, the sheet receiver further includes a pulling device operatively connected to the connecting structure that operatively pulls the sheet into the sheet chamber. More specifically, the pulling device includes a roller rotatably and removably supported within the sheet chamber and generally parallel to the slot. The roller includes a central portion and opposing outer portions. Each first end of the pair of straps is secured to the central portion of the roller via at least one fastener. According to the exemplary embodiment of the invention, the fastener is threaded and extends through the first end and into the roller. Of course, it will be appreciated that any structure or method of securing the straps to the roller may be similarly used.

As the pulling device pulls the sheet into the sheet chamber, the sheet is pulled to wrap about the roller. According to the exemplary embodiment of the invention, engaged attachment of the sheet to the sheet receiver occurs when the sheet sufficiently wraps around the roller to transmit enough torque from the roller to the sheet with enough force to pull the patient. More particularly, the central portion is generally larger in diameter than the opposing outer portions. On one hand, the larger diameter of the central portion transmits torque to the sheet while pulling both the sheet and the patient resting thereon. On the other hand, the reduced diameter of the opposing outer portions accommodates the excess width of the sheet for both the sheet longitudinal sides and the beaded edges during use. As such, most of the force required to pull the patient transmits through the portion of the sheet on the upper surface and about the head end section of the mattress, while less force transmits through the sheet longitudinal sides.

In use, with a patient supported on the sheet and the sheet located on the mattress, this patient repositioning system enables an attendant to cause the sheet and the patient supported thereon to move toward the head end of the mattress, as the sheet is pulled into the slot formed in the housing. Because the sheet has a width that is greater than that of the mattress, and that additional width is retained along opposing longitudinal sides of the mattress, as the sheet moves, and the patient is repositioned the outer portions of the sheet, i.e. the sheet longitudinal sides move from a substantially vertical orientation to a substantially horizontal orientation as the sheet is pulled into the slot. For each sheet, a number of such patient repositionings may occur, until the system indicates via the sheet usage indicia that it is time to replace the sheet. Generally, the attendant causes the sheet to move via operation of the inputs to the drive mechanism, as described above.

To initiate patient repositioning using this system, an attendant places a sheet on the mattress, connects the sheet to the mattress, and also operatively couples the sheet to the drive mechanism. Typically, this connecting of the sheet to the mattress involves securing opposite sheet longitudinal sides of the sheet to oppositely located rows of retainers spaced along the length of the mattress, and the sheet has beaded edges along its longitudinal sides which allow for longitudinal movement of the sheet along the retainers. To operatively couple the sheet to the drive mechanism, the attendant which may also be referred to as an operator, releasably attaches the sheet to the drive mechanism, and the drive mechanism is then used to pull the sheet toward the head end of the mattress, to "bad" the sheet in preparation for subsequent pullings of the sheet toward the head end of the mattress with a patient residing thereon.

With respect to FIG. 3A, the patient 22 is shown after migrating from a head end 48 of the mattress 26 toward a foot end 50 of the mattress 26. In other words, the patient 22 is in the undesirable position with an increased risk of injury and discomfort. The drive mechanism 28 thereby pulls the sheet 16, as indicated by arrow 52, about the head end 48 of the mattress 26, through a slot 54 in the housing 29, and into the sheet receiver 14a. Thereby, the patient 22, resting directly on the sheet 16, is similarly pulled toward the head end 48 of the mattress 26 until the patient 22 reaches the predetermined position.

Figure 4:
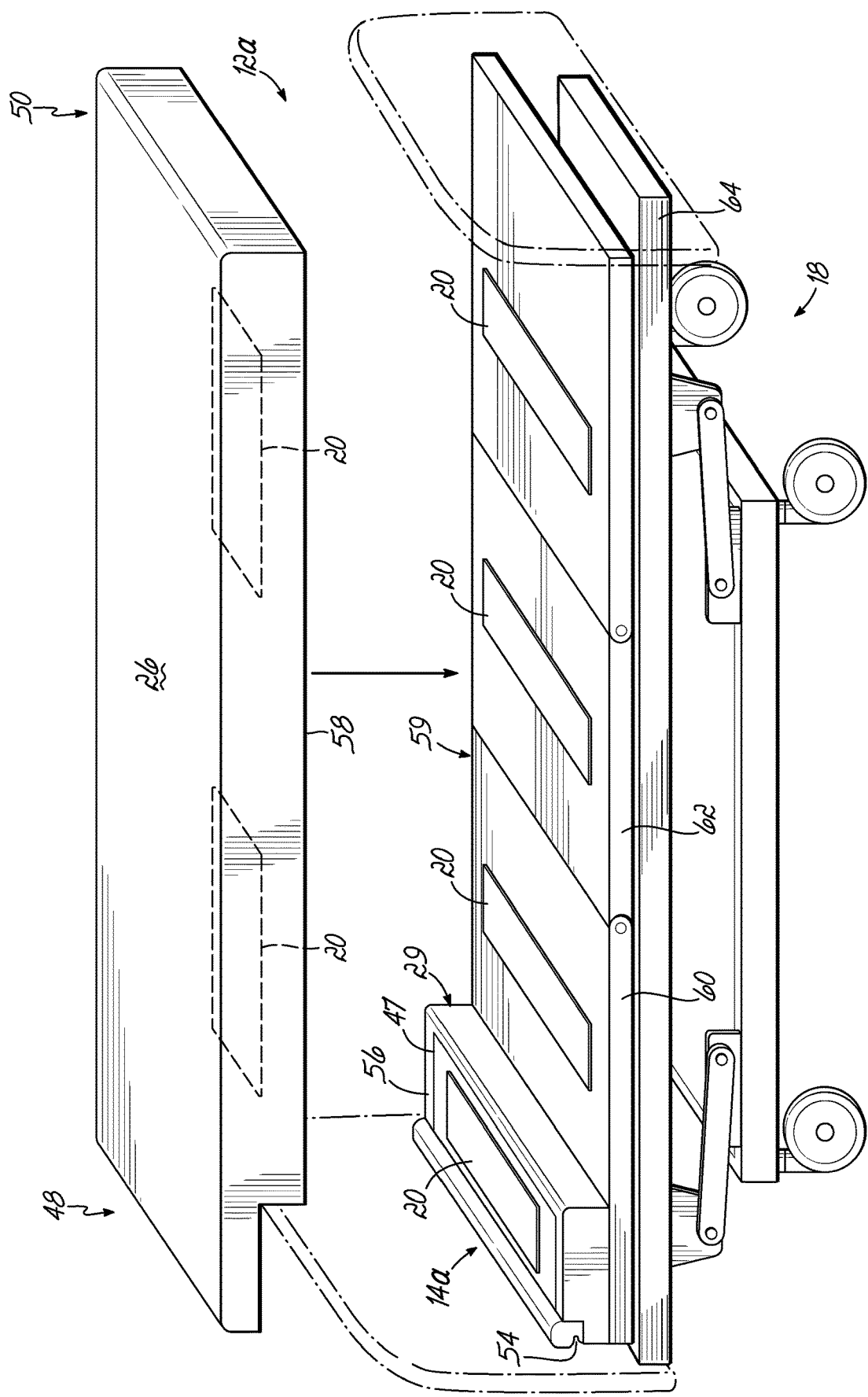
FIG. 4 is a schematic perspective view of the patient monitoring and repositioning system according to the first exemplary embodiment of the invention.

The sensor arrangement 12a configured to sense the position of the patient 22 relative to the mattress 26 is shown in FIG. 4. The sensor arrangement 12a includes the sensors 20 positioned on an upper surface 56 of the housing 29, a lower surface 58 or inner region of the mattress 26, and on a bed deck 59 of the health care bed 18. More particularly, sensors 20 are positioned on respective head and foot ends 48, 50 of the mattress 26 and on a head deck portion 60, a central deck portion 62, and a foot deck portion 64, respectively for sensing the patient's position along substantially the entire top surface of the mattress 26.

Figure 5A:
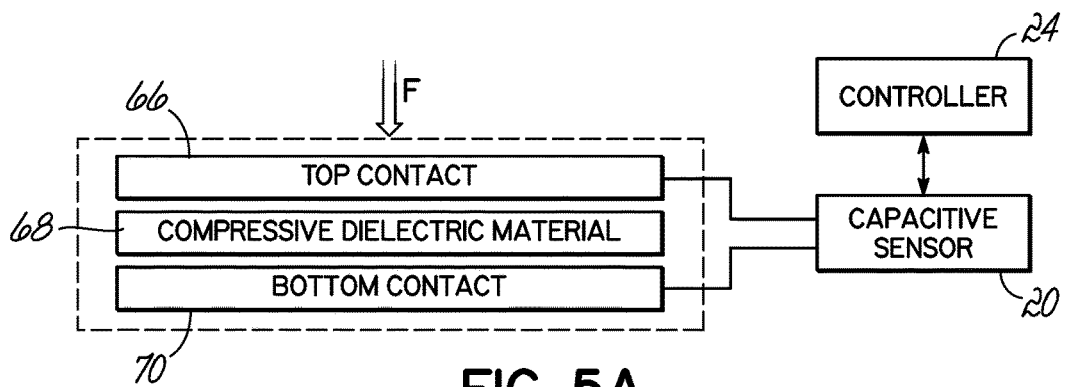
FIG. 5A is a schematic section view of an embodiment of a sensor of the patient monitoring and repositioning system shown in FIG. 4.

The sensor arrangement 12a senses the position of the patient 22 by detecting patient weight along the health care bed 18 and communicating the detected weight to the sheet receiver 14a. As shown in FIG. 5A, each of the sensors 20 is in the form of a capacitive sensor 20. The force F of the patient's weight sandwiches a top contact 66, a compressive dielectric material 68, and a bottom contact 70 together. As such, the capacitive sensor 20 detects a change in capacitance value for communication to the controller 24. The controller 24 collects the information from each of the sensors 20, analyzes the collective information regarding the weight distribution of the patient 22 as detected by the sensors 20, and determines the patient position based on detected capacitance from the entirety of the sensor arrangement 12a.

Figure 5B:
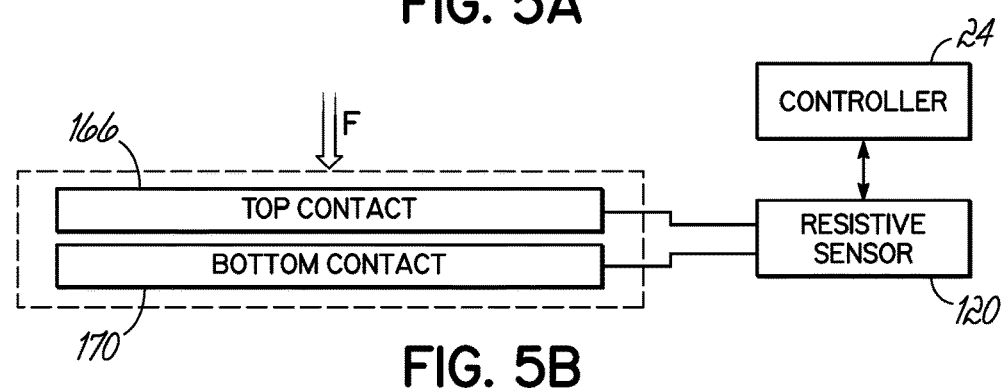
FIG. 5B is a schematic section view of another embodiment of a sensor of the patient monitoring and repositioning system shown in FIG. 4.

According to another exemplary embodiment shown in FIG. 5B, a sensor 120 is in the form of a resistive sensor 120. The force F of the patient's weight directs a top contact 166 against a bottom contact 170. As such, the resistive sensor 120 detects a change in resistance value for communication to the controller 24. The controller 24 collects the information from each of the sensors 120, analyzes the collective information regarding the weight distribution of the patient 22 as detected by the sensors 120, and determines the patient position based on detected resistance from the entirety of the sensor arrangement 112a.

Figure 6:
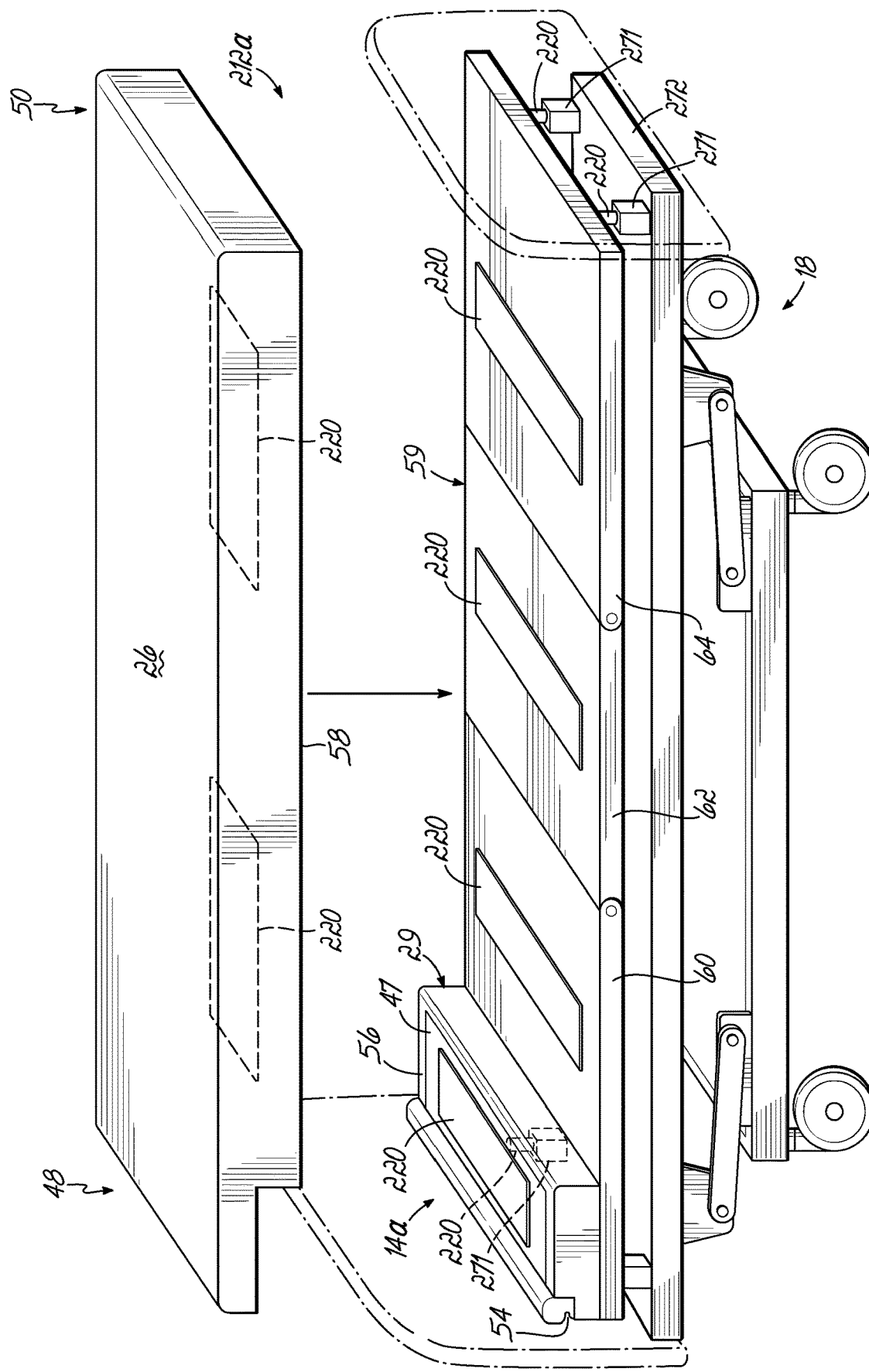
FIG. 6 is a schematic perspective view of a patient monitoring and repositioning system according to a second exemplary embodiment of the invention.

FIG. 6 shows a second embodiment of a sensor arrangement 212a integrated within the health care bed 18. The sensor arrangement 212a includes a plurality of sensors 220, which are each in the form of strain gauges 220. The force of the patient's weight effectively bends the strain gauge 220 so as to change a resistance value of the strain gauge 220. As such, the strain gauge 220 detects the changing resistance values for communication to the controller 24. In addition, strain gauges 220 have been included on pedestals 271 positioned between the bed deck 59 and a remaining frame 272 of the health care bed 18 supporting the bed deck 59 thereon. The controller 24 collects the information from each of the sensors 220, analyzes the collective information regarding the weight distribution of the patient 22 as detected by the sensors 220, and determines the patient position based on detected resistance values from the entirety of the sensor arrangement 212a.

Figure 8A:
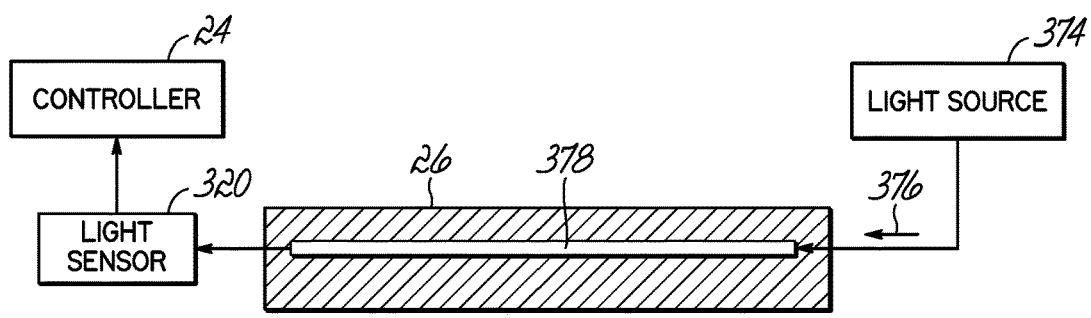
FIG. 8A is a schematic section view of a sensor of the patient monitoring and repositioning system shown in FIG. 7.
Figure 8B:
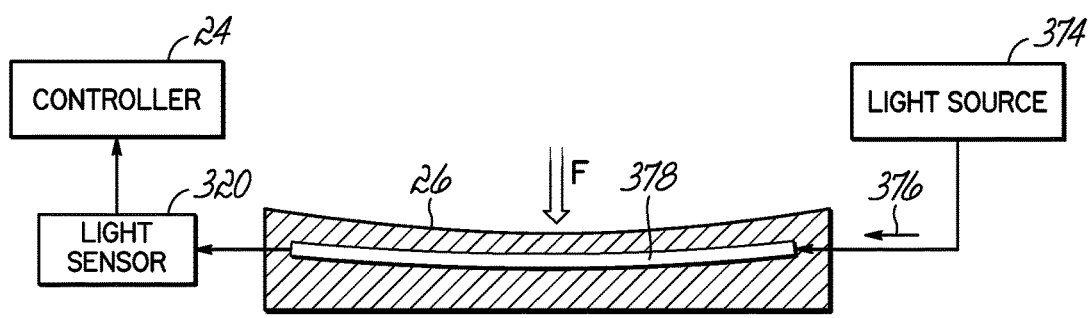
FIG. 8B is a schematic section view of the sensor shown in FIG. 8A depressed by a force of a patient thereon.
Figure 7:
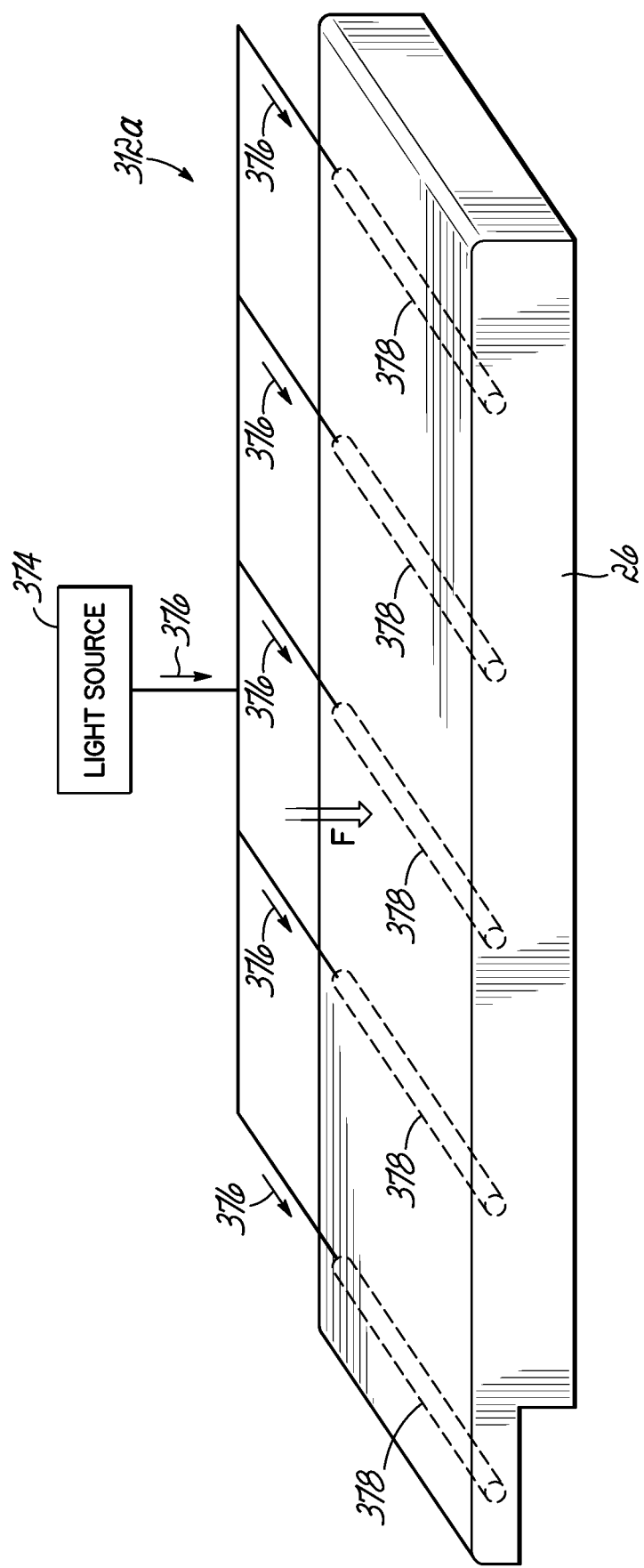
FIG. 7 is a schematic perspective view of a patient monitoring and repositioning system according to a third exemplary embodiment of the invention.

A third exemplary embodiment of a sensor arrangement 312a is shown in FIGS. 7-8B. The sensor arrangement 312a includes a plurality of sensors 320, which are each in the form of a light sensor 320. A light source 374 directs light, as indicated by arrows 376, along fiber-optic cable 378. The force F of the patient's weight effectively bends the fiber-optic cable 378 so as to change an amount of light passing through the fiber-optic cable 378. As such, the light sensor 320 detects the changing light values for communication to the controller 24. The controller 24 collects the information from each of the sensors 320, analyzes the collective information regarding the weight distribution of the patient 22 as detected by the sensors 320, and determines the patient position based on detected light from the entirety of the sensor arrangement 312a.

Figure 9:
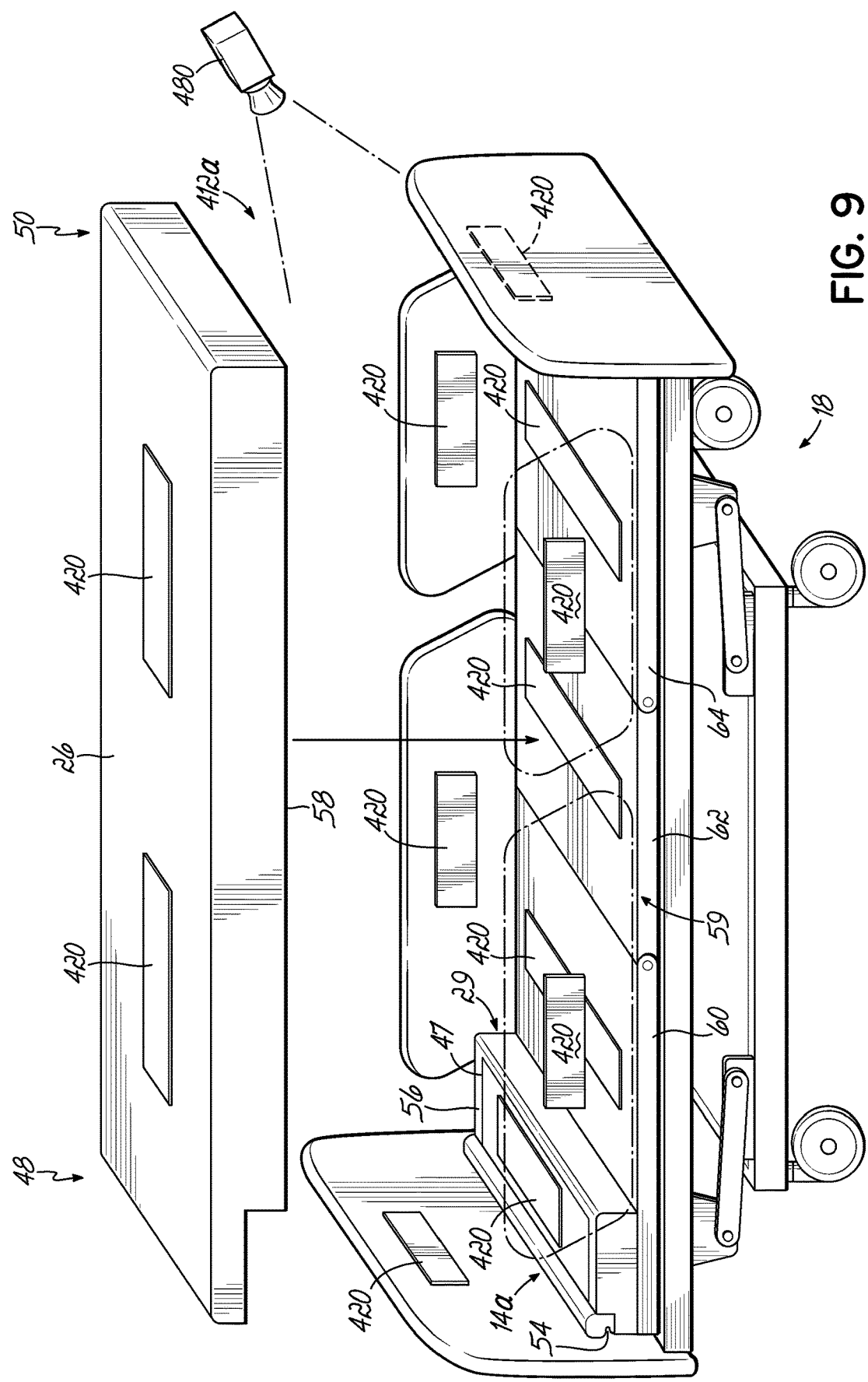
FIG. 9 is a schematic perspective view of a patient monitoring and repositioning system according to a fourth exemplary embodiment of the invention.

A fourth exemplary embodiment of a sensor arrangement 412a is shown in FIG. 9. The sensor arrangement 412a includes a plurality of sensors 420, which are each in the form of an optical sensor 420. Generally, the optical sensors 420 work in opposing pairs such that an infrared beam (not shown) is directed therebetween. The presence of the patient 22 between the pair of optical sensors 420 interrupts the infrared beam so as to indicate the position of the patient 22. As such, the optical sensors 420 detect the changing infrared beam for communication to the controller 24. The controller 24 collects the information from each of the sensors 420, analyzes the collective information regarding blockage and/or non-blockage of the infrared beams by the patient 22 as detected by the sensors 420, and determines the patient position based on the detected infrared beams from the entirety of the sensor arrangement 412a.

In addition, the sensor arrangement 412a further includes a camera 480 positioned proximate to the mattress 26 for viewing the patient 22 on the mattress 26. For example, the camera 480 may be attached to the health care bed 18 or on a surface within the facility, such as a head wall, foot wall, ceiling, or other location proximate to the bed 18. The camera 480 visually collects light representing the patient 22 and directs the representation to the controller 24. The controller 24 is further configured to analyze the representation and identify the position of the patient 22 relative to the mattress 26.

This specification shows and describes several embodiments of the invention. However, those skilled in the art will appreciate that the disclosed embodiments are susceptible to a reasonable amount of modification and/or permutation, without departing from the overall scope of the invention. By way of example, the operative connections described herein may be either wired or wireless. Any number, locations, and combination of sensors 20, 120, 220, 320, 420 may be used in accordance with the invention discussed herein. For example, one of the sensor arrangements 412a, such as the camera 480, may be used in combination with any of the other sensors 20, 120, 220, 320. By way for further example, fewer sensors 20, 120, 220, 320, 420 may be more cost effective in some applications, whereas more sensors 20 may provide better resolution of the patient's position in other applications. Furthermore, the actual conversion of the individual sensor 20, 120, 220, 320, 420 outputs may be accomplished by controller 24 or a separate additional controller dedicated to only performing the patient 22 position calculation. This additional controller would then communicate the position of the patient 22 to controller 24 using a wired or wireless communication path. Furthermore, the reference to the "sensors" is not intended to limit the invention only to the sensors 20, 120, 220, 320, 420 shown and described herein. Rather, any sensor capable of detecting the position of the patient 22 (e.g., magnetic sensing of heart location, fluid flow detection within the body and hence location of organs by acoustic/Doppler/ultrasonic detection of location of major organs, etc.), in whole or in part, may be used in accordance with the invention described herein.

What is claimed is:

1. A patient monitoring and repositioning system in combination with a bed having a deck, comprising:
   a mattress residing on the deck and having a head end, a foot end, and an upper surface;
   a sheet residing on the upper surface;

a drive mechanism located near the head end of the mattress and operable to pull the sheet toward the head end of the mattress to thereby reposition the sheet relative to the mattress, and also reposition a patient residing on the sheet toward the head end of the mattress, the sheet maintaining contact with the upper surface of the mattress while the sheet is being repositioned relative to the mattress;

a housing containing the drive mechanism, the housing including a slot extending therealong, and the drive mechanism being operable to pull the sheet into the housing via the slot;

a sensor operatively connected to the drive mechanism, the sensor adapted to sense a position of the patient relative to the mattress on the bed and to generate a signal in response to the patient moving from a predetermined position;

a controller operatively connected to the drive mechanism and the sensor; and a safety interlock operatively connected to the controller, wherein the controller prevents the patient from being repositioned if the safety interlock detects at least one of the following conditions: a bed head deck angle is too high, the sheet is improperly loaded, the absence of the patient on the mattress, and sheet contamination.

2. The patient monitoring and repositioning system of claim 1 wherein the sensor is adapted to determine the patient's translational position relative to the mattress, the patient's rotational position relative to the mattress, or any combination thereof.

3. The patient monitoring and repositioning system of claim 1 further comprising:
an indicator operatively connected to the sensor, wherein the indicator indicates the patient was repositioned.

4. The patient monitoring and repositioning system of claim 1 wherein the housing further includes an access door movable relative to the housing to thereby permit access to the inside of the housing.

5. The patient monitoring and repositioning system of claim 1 wherein the controller prevents the patient from being repositioned if the safety interlock detects the access door is open.

6. The patient monitoring and repositioning system of claim 1 wherein the controller is located on at least one of the housing and the bed and is operatively connected to a user interface, wherein the controller is operative to receive an input from the patient via the user interface to cause the drive mechanism to reposition the patient.

7. A plurality of the patient monitoring and repositioning systems of the type described in claim 1 and further comprising:
a central control system operatively connected to the controllers of the plurality of patient monitoring and repositioning systems, for monitoring the positions of a plurality of patients located respectively on a plurality of beds, thereby for each of the patient monitoring and repositioning systems to enable the ongoing monitoring of at least one of: the patient not in the predetermined position, a time that the patient is not in the predetermined position, an amount of patient repositionings, a frequency of patient repositionings in a facility, an amount of the sheet already used, a need to change or reset the sheet on the bed, a distance migrated by the patient on the bed, a time of the patient in each position on the bed, a time delay before repositioning the patient on the bed, a duration of repositioning the patient on the bed, the position of the patient on the bed, a time of day the patient was repositioned, and a frequency of patient repositionings executed on the bed.

8. The plurality of patient monitoring and repositioning systems of claim 7 wherein the central control system is adapted to complete at least one of: provide indications of patient position to one or more caregivers, verify automatic repositioning of the patients by the plurality of patient monitoring and repositioning systems, verify repositionings of the patient by the caregiver located at the bedside, and direct the plurality of patient monitoring and repositioning systems to perform patient repositionings.

9. A system, comprising:
a patient monitoring and repositioning system in combination with a bed having a deck, comprising:
a mattress residing on the deck and having a head end, a foot end, and an upper surface;
a sheet residing on the upper surface;
a drive mechanism located near the head end of the mattress and operable to pull the sheet toward the head end of the mattress to thereby reposition the sheet relative to the mattress, and also reposition a patient residing on the sheet toward the head end of the mattress, the sheet maintaining contact with the upper surface of the mattress while the sheet is being repositioned relative to the mattress;
a housing containing the drive mechanism, the housing including a slot extending therealong and the drive mechanism being operable to pull the sheet into the housing via the slot;
a sensor operatively connected to the drive mechanism, the sensor adapted to sense a position of the patient relative to the mattress on the bed and to generate a signal in response to the patient moving from a predetermined position; and
a controller operatively connected to the drive mechanism and the sensor; and
a central control system operatively connected to the controller for monitoring the position of the patient located on the bed to enable the ongoing monitoring of at least one of: the patient not in the predetermined position, a time that the patient is not in the predetermined position, an amount of patient repositionings, a frequency of patient repositionings in a facility, an amount of the sheet already used, a need to change or reset the sheet on the bed, a distance migrated by the patient on the bed, a time of the patient in each position on the bed, a time delay before repositioning the patient on the bed, a duration of repositioning the patient on the bed, the position of the patient on the bed, a time of day the patient was repositioned, and a frequency of patient repositionings executed on the bed.

10. The system of claim 9, further comprising:
a plurality of the patient monitoring and repositioning systems,
wherein the central control system is operatively connected to the controllers of the plurality of patient and monitoring and repositioning systems, for monitoring the positions of a plurality of patients located respectively on a plurality of beds.

11. The system of claim 10 wherein the central control system is adapted to complete at least one of: provide indications of patient position to one or more caregivers, verify automatic repositioning of the patients by the plurality of patient monitoring and repositioning systems, verify repositionings of the patient by the caregiver located at the bedside, and direct the plurality of patient monitoring and repositioning systems to perform patient repositionings.

12. The patient monitoring and repositioning system of claim 9 wherein the housing further includes an access door movable relative to the housing to thereby permit access to the inside of the housing.

13. A method of monitoring and repositioning a sheet that is located on a mattress, the mattress having a head end and a foot end and being supported by a bed frame, comprising:
- causing the sheet and a patient supported thereon to move toward the head end of the mattress, whereby the causing further includes pulling the sheet into a slot formed in a housing located adjacent the head end and within a footprint of the mattress, the housing including an access door movable relative to the housing to an open position to permit access to the inside of the housing, the access door being located within the footprint of the mattress, the sheet being retained along opposing longitudinal sides of the mattress;
- prior to the causing, sensing a position of the patient and determining that the sensed position of the patient differs from a predetermined position on the mattress;
- preventing the patient from being moved toward the end of the mattress if a safety interlock detects at least one of the following conditions: a bed head deck angle is too high, the sheet is improperly loaded, the absence of the patient on the mattress, and sheet contamination; and
- after the causing, determining that the patient is in the predetermined position.

14. The method of claim 13 further comprising:
monitoring, via a controller, the sensing and the causing.

15. The method of claim 14 wherein the controller is located proximate to the mattress and is capable of automatically repositioning the patient.

16. The method of claim 14 wherein the controller is located in a room without the mattress and communicates therewith via a wired or a wireless connection.

17. The method of claim 13 wherein a central controller operatively connects to a plurality of controllers, each of the controllers respectively associated with a different patient monitoring and repositioning system, the central controller being positioned in a room without the different patient monitoring and repositioning systems, and further comprising:

using the central controller to monitor at least one of the following:
- the positions of a plurality of patients located respectively on a plurality of beds, thereby for each of the different patient monitoring and repositioning systems to enable the ongoing monitoring of at least one of: the patient not in the predetermined position, a time that the patient is not in the predetermined position, an amount of patient repositionings, a frequency of patient repositionings in a facility, an amount of sheet already used, a need to change or reset the sheet on the bed, a distance migrated by the patient on the bed, a time of the patient in each position on the bed, a time delay before repositioning the patient on the bed, a duration of repositioning the patient on the bed, the position of the patient on the bed, a time of day the patient was repositioned, and a frequency of patient repositionings executed on the bed.

* * * * *